(12) United States Patent
Shih et al.

(10) Patent No.: US 7,579,436 B2
(45) Date of Patent: Aug. 25, 2009

(54) PEPTIDE COMPOUND FOR MEASURING SULFUR COMPOUND AND AMMONIA

(75) Inventors: Pei-Ching Shih, Changhua (TW); Pei-Shin Jiang, Taichung (TW); Wen-Hsun Kuo, Tainan (TW); Yuh-Jiuan Lin, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 89 days.

(21) Appl. No.: 11/681,094

(22) Filed: Mar. 1, 2007

(65) Prior Publication Data
US 2008/0114152 A1 May 15, 2008

Related U.S. Application Data

(62) Division of application No. 10/321,652, filed on Dec. 18, 2002, now Pat. No. 7,267,989.

(30) Foreign Application Priority Data
Dec. 26, 2001 (TW) .............................. 90132419 A

(51) Int. Cl.
*C07K 7/06* (2006.01)

(52) U.S. Cl. .................. 530/328; 530/329; 530/330
(58) Field of Classification Search .................. None
See application file for complete search history.

(56) References Cited

U.S. PATENT DOCUMENTS

| | | | |
|---|---|---|---|
| 6,712,770 B2 | 3/2004 | Lin et al. | |
| 7,060,458 B1 * | 6/2006 | Doucette-Stamm et al. | 435/69.1 |
| 7,267,989 B2 * | 9/2007 | Shih et al. | 436/86 |

OTHER PUBLICATIONS

Spinelli et al. The Structure of the Monomeric Porcine Odorant binding Protein . . . Biochemistry. 1998, vol. 37, No. 22, pp. 7913-7918.*

* cited by examiner

*Primary Examiner*—Jeffrey E Russel
(74) *Attorney, Agent, or Firm*—Sughrue Mion, PLLC

(57) ABSTRACT

A peptide compound for measuring sulfur compound and ammonia and measurement method and device using the compound. The method comprises contacting an analyte with a sensory device coated with the peptide compound to produce a signal, processing the signal to produce a result, and comparing the result with a database to define the presence of the sulfur compound and ammonia in the analyte.

1 Claim, 2 Drawing Sheets

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Gly Asn Thr Tyr Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Glu Gly Asn Thr Tyr Asp
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3
```

```
Lys Phe Lys Glu Val
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Glu Ser Lys Val Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Asp Val Asn Tyr Gly Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Lys Phe Lys Glu Val Thr Arg Glu Asn
1               5
```

PEPTIDE COMPOUND FOR MEASURING SULFUR COMPOUND AND AMMONIA

CROSS REFERENCE TO RELATED APPLICATIONS

This application is a Divisional of pending U.S. patent application Ser. No. 10/321,652, filed Dec. 18, 2002 and entitled "Method and device for measuring sulfur compound and/or ammonia based on a sensory unit coated with at least one novel peptide".

BACKGROUND OF THE INVENTION

1. Field of the Invention

The present invention relates to a peptide compound; more particularly, the present invention relates to a peptide compound having high sensitivity and potent binding ability to sulfur compound and ammonia exhaled from cirrhosis patients. The present invention also relates to a method for measuring sulfur compound and/or ammonia with the peptide compound.

2. Description of the Related Art

In the olfactory system of mammals, the olfactory receptors are embedded in cell membrane of the nasal mucosa. The olfactory receptors react with odor molecules and the signals produced from the reaction transducer to the olfactory region, a brain structure for odor determination, by serial biochemical reactions. The olfactory receptors respond to different odor molecules with unique binding regions. The binding specificity is determined by the amino acid sequence and the tertiary structure of the olfactory receptor. Based on this concept, the present invention suggests that different peptide sequences have unique binding abilities to different odor molecules or compounds. It is, therefore, an object of the present invention to design different peptide compounds as receiving membrane for the measurement of specific compounds in accordance with different measurement purposes.

Additionally, certain disorders, such as cirrhosis, liver disease, or gingivitis, may raise the sulfide level in the body. Nephrosis, uremia, or gastric ulcer may raise the ammonia level of the body. Measuring the level of sulfur compound and/or ammonia in the body or by exhalations can determine whether the subject has these kind of disorders.

In addition, spoiled seafood and fish release ammonia. Another application of the present invention is thus the detection of seafood freshness.

Similarly, the present invention is also useful for measuring sulfur compound and/or ammonia in air and water to determine levels of pollution thereof.

BRIEF SUMMARY OF INVENTION

A detailed description is given in the following embodiments with reference to the accompanying drawings.

It is therefore a primary object of the present invention to provide a peptide compound having high sensitivity and potent binding ability to sulfur compound and/or ammonia, and suitable for measuring sulfur compound and/or ammonia. In application, the peptide compound of the present invention is suitable for measuring exhalations from cirrhosis patients.

One aspect of the invention provides a method for measuring sulfur compound and/or ammonia with the peptide compound. The method comprises contacting an analyte with at least one peptide compound coated on a sensory device to produce a signal; processing the signal to produce a result by comparing the result with a database to define the presence of sulfur compound and/or ammonia in the analyte.

Another aspect of the invention provides a device for measuring sulfur compound and/or ammonia. The device includes one or more sensory units coated with the peptide compound, and a signal processing unit coupled with the sensory unit to produce a signal.

The peptide sequence of the invention features high sensitivity and potent binding ability to sulfur compound and/or ammonia. Using the peptide sequence or peptide-containing compound as a receptor for low-olfactory-threshold sulfur compound and/or ammonia, the measurement for sulfur compound and/or ammonia can be performed with higher sensitivity and is suitable for analytes of low concentration.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

Based on the secondary structure of protein analyzed for peptides sequence features, the tertiary structure of protein for the simulation of protein binding site to target molecule, or the combination of amino acid designed by the physical and chemical features of analytes, the peptide compound for measuring sulfur compound is designed and artificially synthesized. Using the peptide sequence, the sensory device or chip produces signals responding to sulfur compound, i.e. compounds having a functional group of —R—SH; wherein the R is alkyl group or aryl group. Especially, the measurement is more sensitive for ammonia, dimethylsulfide, or dimethylsulfide:$H_2O$=1:1.

The peptide compound of the present invention is:

```
Sequence ID No.1:  Gly-Asn-Thr-Tyr-Asp;

Sequence ID No.2:  Glu-Gly-Asn-Thr-Tyr-Asp;

Sequence ID No.3:  Lys-Phe-Lys-Glu-Val;

Sequence ID No.4:  Glu-Ser-Lys-Val-Tyr;

Sequence ID No.5:  Asp-Val-Asn-Tyr-Gly-Asn;
or

Sequence ID No.6:  Lys-Phe-Lys-Glu-Val-Thr-Arg-Glu-
                   Asn.
```

One or a plurality of modified functional groups can be added at the carboxylic end and/or amino end of the peptide compound as needed. The modified functional group includes amino acids or other functional group. The amino acids include, but are not limited to, alanine, arginine, asparagine, aspartic acid, cystein, glutamine, glutamic acid, glycine, histidine, isoleucine, leucine, lysine, methionine, phenylalanine, proline, serine, threonine, tryptophan, tyrosine, and valine. The functional group includes, but is not limited to, COOH, —NH2, —CHO, —OH, or —SH.

Figure 1:
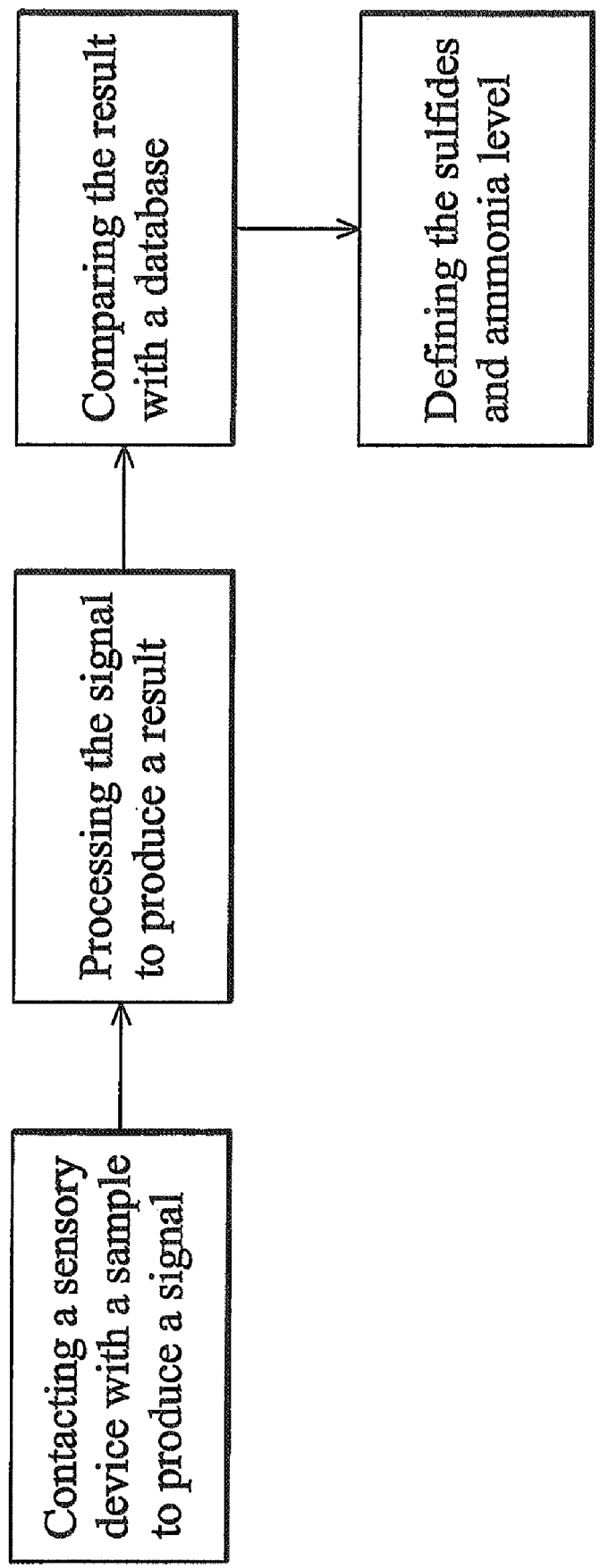
FIG. 1 is a flowchart showing the process of the method for measuring sulfur compound and ammonia with the peptide compound of the invention.

The method for measuring sulfur compound and/or ammonia with the peptide compound of the invention features the binding ability of the peptide compound to sulfur compound or ammonia to obtain the measurement of sulfur compound, and ammonia in liquid or volatile gas phase in an analyte. FIG. 1 is a flowchart showing the method for measuring sulfur compound and ammonia with the peptide compound of the invention. The method comprises the steps of contacting an analyte with a sensory device coated with the peptide compound to produce a signal; processing the signal to produce a result; and comparing the result with an established database to define the presence or the level of sulfur compound and ammonia. The sulfur compound are compounds having a functional group of —R—SH, wherein the R is alkyl group or aryl group, for example, dimethylsulfide or a compound having ammonia group or a ratio of dimethylsulfide:$H_2O$=1:1. The method comprises the steps of immobilizing the peptide compound on the sensory device, contacting the sensory device with an analyte, and detecting the binding of the peptide compound and sulfur compound or ammonia to measure the presence of the sulfur compound and/or ammonia in the analyte. The sensory device includes, but is not limited to, chemical sensor, biosensor or electric nose, biochip; the transducer of the sensory device includes, but is not limited to, piezoelectric quartz crystal, surface acoustic wave, electrochemical, fiber optic, surface plasmon resonance, or metallic oxide semiconductor. Piezoelectric crystal is a valuable measurement device including a quartz crystal coated with the peptide compound. The reaction of the peptide compound and the sulfide molecule induce a mass change and the change interferes with the frequency of the quartz crystal. The potency of the reaction can be measured according to the frequency change of the quartz crystal. The peptide compound of the present invention is sensitive and has a potent binding ability to sulfur compound and/or ammonia, thereby providing a measurement for sulfur compound and/or ammonia with high sensitivity. In one embodiment of the present invention, the analyte is gas, liquid, or solid. For example, the analyte is air, water, seafood, blood, urine, sweat, or exhalations from a subject.

The method for measuring sulfur compound and/or ammonia in the present invention can be applied in a wide range of fields. In one embodiment, the measurement of sulfur compound level in exhalations, blood, sweat, or urine of a subject can be used for diagnosing the presence of a disorder in the subject. The disorders include but are not limited to cirrhosis, liver diseases, or gingivitis. In another embodiment, the measurement of ammonia level in exhalations, blood or urine of a subject can be used for diagnosing the presence of disorders in the subject. The disorders include, but are not limited to, nephrosis, uremia or gastric ulcer. In particular, cirrhosis can be diagnosed directly from the measurement of sulfur compound and/or ammonia level in exhalations of the subject. The method of the present invention can also be applied in seafood freshness detection, air pollution, and water quality detection.

The device for measuring sulfur compound and/or ammonia in the present invention includes a sensory unit coated with the peptide compound, and a signal processing unit coupled therewith to produce a signal. The sensory unit includes, but is not limited to, the above mentioned transducers or biochips.

Without intending to limit it in any manner, the present invention will be further illustrated by the following examples.

EXAMPLE

The design of the electric nose system used herein is described as follows.

Using the tertiary structure of olfactory receptor as a model, computer software, Insight II, was used to simulate the potential peptide compounds able to bind to sulfur compound or ammonia in the exhalations of cirrhosis patients. The peptide compounds were modified according to the features of amino acids. The designed peptide compounds specific and sensitive to sulfur compound and/or ammonia were then used as the receiving membrane of the electric nose. The transducer of the electric nose is a piezoelectric quartz crystal coated with the designed peptide compound. The electric nose system is used for analyzing the response of the peptide compound to sulfur compound.

Preparation 1: Synthesis of Peptide Compound

The peptide compounds of the invention can be obtained artificially, for example, by solid phase synthesis, liquid peptide compound synthesis, enzymatic synthesis, or recombinant DNA technology. Solid phase synthesis was applied using Wang resin as resin and F-moc as protecting group. The synthesis was performed by 432A Peptide Synthesizer (Apply Biosystems, USA).

Preparation 2: Modification and Coating of the Peptide Compound onto the Piezoelectric Quartz Crystal The peptide compounds were designed having stable covalent bond with Au. The peptide compounds were sulfurated by Traut's reagent. The sulfurated peptide compounds were then diluted with suitable organic solvent according to the solubility of the peptide compounds. The peptide compound solutions were coated on the Au electrode surface of the piezoelectric quartz crystal. After 45 reaction, the frequency was reduced to 15000~20000 Hz.

Preparation 3: Preparation of Volatile Gas

Dimethylsulfide, ammonia, acetone, butyric acid, and formaldehyde in reagent grade were dissolved in 5 mL of volatile organic solvent and then placed in 120 mL of sealed serum bottles separately. After 5 days balancing, the saturated status of vapor pressure was reached. The concentration of the volatile gases can be measured according to the concentration of the solution and the saturated vapor pressure. The volatile gases can be diluted or directly used for analysis as needed.

Example 1

Response of Peptides No. 1-6 to the Volatile Gases

The piezoelectric crystal of the electric nose was coated with the peptides of sequence ID No. 1. The electric nose system (Smart Biotechnology Co., Ltd., Taipei, Taiwan) was applied to react with volatile gases of dimethylsulfide, dimethylsulfide:$H_2O$=1:1, ammonia, and the mixture thereof separately. The analyte gases were in a volume of 5 mg/L. The specificity and sensitivity were compared.

The amount of the six peptides coated on the piezoelectric crystal of the electric nose is based on Sauerbrey equation (Sauerbrey, 1959) that the increase in mass is proportional to the frequency decrease, and the frequency decrease (Hz) after the peptide compound coating represents the amount of peptide compound. In this example, the amount of the peptide compounds with sequence ID No. 1-6 were listed in table 1.

TABLE 1

| Seq ID No. | 1 | 2 | 3 | 4 | 5 | 6 |
|---|---|---|---|---|---|---|
| Amount of coated peptide compounds (Hz) | 6442 | 731 | 4890 | 8750 | 883 | 1148 |

Figure 2:
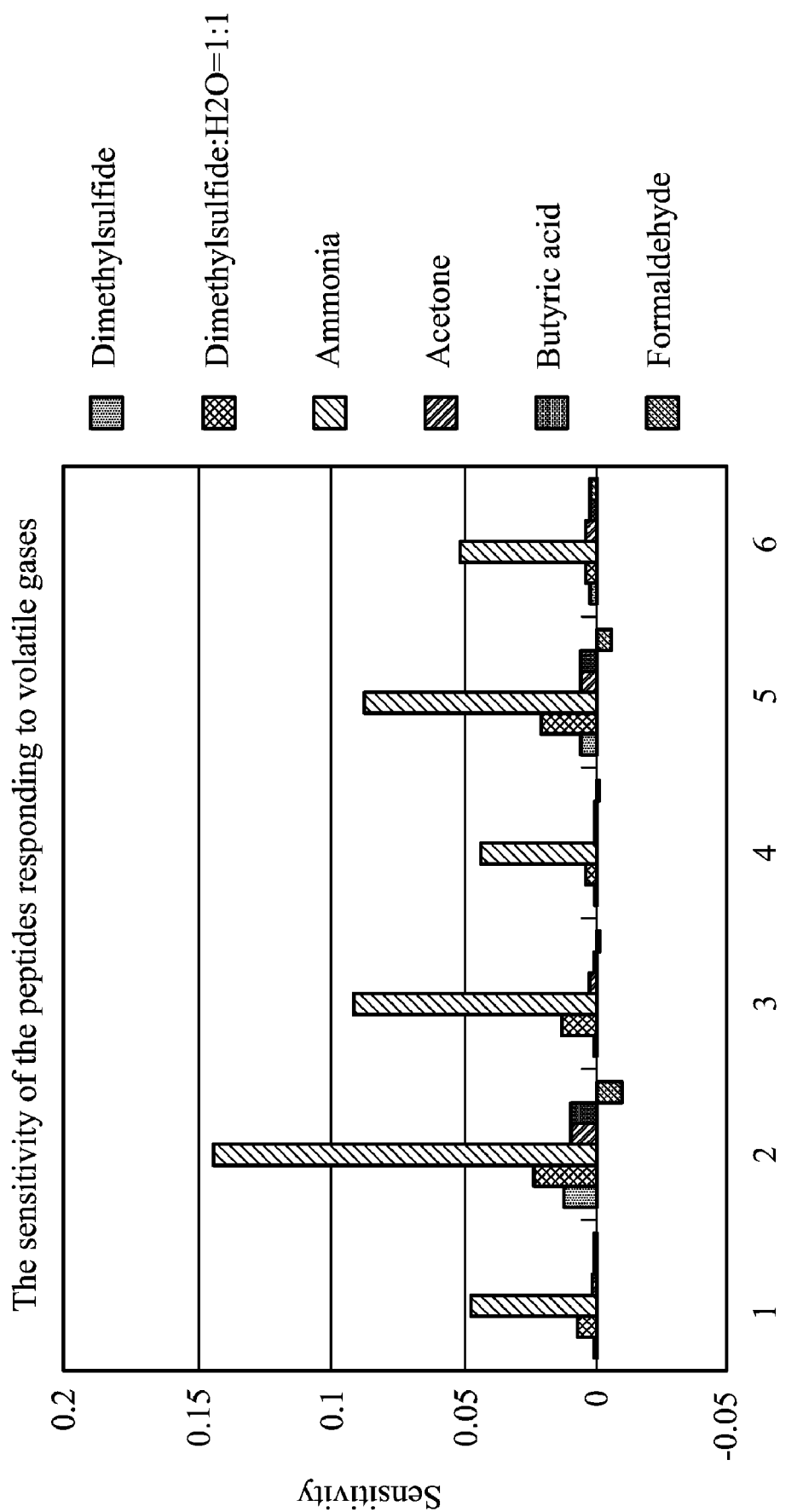
FIG. 2 is a diagram showing the sensitivity of peptide sequences ID No. 1-6 to various organic volatile gases.

The sensitivities of the peptide compounds with sequence ID No. 1-6 responding to dimethylsulfide, ammonia, acetone, butyric acid, and formaldehyde are shown in FIG. 2. The results show that the peptide compounds of sequence ID No. 1 and 2 have significant responses and higher specificity to dimethylsulfide, dimethylsulfide:$H_2O$=1:1, and ammonia, especially ammonia. All of the peptide compounds have poor responses to the other organic volatile gases. The results indicate that the peptide compounds of sequence ID No. 1 and 2 are suitable for measuring sulfur compound and/or ammonia. The peptide compounds of sequence ID No. 3-6 have significant responses and higher specificity to dimethylsulfide:$H_2O$=1:1 and ammonia, and this indicates that the peptide compounds of sequence ID No. 3-6 are suitable for measuring dimethylsulfide:$H_2O$=1:1 and ammonia.

Example 2

Responses of Peptide Compounds with Sequence ID No. 1-6 Healthy Subject Exhalation The exhalations from cirrhosis patients contains large amounts of sulfur compound and ammonia. Exhalations from 63 cirrhosis patients and 31 non-cirrhosis-affected subjects at Chinese Medical College was collected and measured by the electric nose system with the six peptide compounds of the invention, separately. The results were analyzed by statistic software, STATGRAPHICS Plus. The analyzed results show that 60 (95.24%) of the 63 cirrhosis patients were diagnosed with cirrhosis, with 3 (4.76%) of them diagnosed as normal; 3 (9.68%) of the 31 non-cirrhosis-affected subjects were diagnosed with cirrhosis, and 28 (90.32%) as normal. According to the analysis, the method of the invention has an accuracy of 93.62%. It is obvious that the peptide compounds of the present invention are valuable for the diagnosis of cirrhosis.

In a similar process, the present invention is also suitable for establishing a database to diagnose nephrosis, uremia, liver diseases, gingivitis, or gastric ulcer.

While the invention has been particularly shown and described with the reference to the preferred embodiments thereof, it will be understood by those skilled in the art that various changes in form and details may be made without departing from the spirit and scope of the invention.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A peptide compound, consisting of a peptide sequence of:

Gly-Asn-Thr-Tyr-Asp,
(SEQ ID NO:1)

Glu-Gly-Asn-Thr-Tyr-Asp,
(SEQ ID NO:2)

Lys-Phe-Lys-Glu-Val,
(SEQ ID NO:3)

Glu-Ser-Lys-Val-Tyr,
(SEQ ID NO:4)

Asp-Val-Asn-Tyr-Gly-Asn,
(SEQ ID NO:5)
or

Lys-Phe-Lys-Glu-Val-Thr-Arg-Glu-Asn,
(SEQ ID NO:6)

or a mixture of the peptide compounds.

* * * * *